United States Patent
Campbell

[19]

[11] Patent Number: 6,102,945
[45] Date of Patent: Aug. 15, 2000

[54] SEPARABLE ANNULOPLASTY RING

[75] Inventor: Louis A. Campbell, Austin, Tex.

[73] Assignee: Sulzer Carbomedics, Inc., Austin, Tex.

[21] Appl. No.: 09/174,386

[22] Filed: Oct. 16, 1998

[51] Int. Cl.[7] .................................................. A61F 2/24
[52] U.S. Cl. ...................................... 623/2.37; 623/2.36
[58] Field of Search ............................. 623/2, 2.36, 2.37

[56] References Cited

U.S. PATENT DOCUMENTS

| | | | |
|---|---|---|---|
| 3,656,185 | 4/1972 | Carpentier | 3/1 |
| 4,042,979 | 8/1977 | Angell | 3/1.5 |
| 4,055,861 | 11/1977 | Carpentier | 3/1.5 |
| 4,144,046 | 3/1979 | Esposito | 71/86 |
| 4,164,046 | 8/1979 | Cooley | 3/1.5 |
| 4,290,151 | 9/1981 | Massana | 3/1.5 |
| 4,489,446 | 12/1984 | Reed | 3/1.5 |
| 5,061,277 | 10/1991 | Carpentier et al. | 623/2 |
| 5,104,407 | 4/1992 | Lam et al. | 623/2 |
| 5,306,296 | 4/1994 | Wright et al. | 623/2 |
| 5,593,424 | 1/1997 | Northrup, III | 606/232 |
| 5,716,397 | 2/1998 | Myers | 623/2 |

FOREIGN PATENT DOCUMENTS

WO 99/29269   6/1999   WIPO .

OTHER PUBLICATIONS

St June Medical Product Literature, SIM Tailor™ Annuloplasty Ring.

*Primary Examiner*—Michael J. Milano
*Attorney, Agent, or Firm*—Timothy L. Scott; Philip S. Lyren; Kenneth S. Barrow

[57] ABSTRACT

A support ring for a natural human heart valve includes a first ring portion having opposite terminal ends and a second ring portion having opposite terminal ends. An interconnector extends through and interconnects the first and second ring portions, to maintain the opposite terminal ends of the first ring portion adjacent the opposite terminal ends of the second ring portion, to form a segmented ring having a first and a second interface between the first and second ring portions. The first ring portion is of a greater length than the second ring portion. The ring portions are separable by severing the interconnector at the first and second interfaces, thus producing two variable size ring segments.

17 Claims, 4 Drawing Sheets

SEPARABLE ANNULOPLASTY RING

BACKGROUND

The disclosures herein relate generally to annuloplasty rings and more particularly to an annuloplasty ring which is formed by two separable portions so that the entire ring or a separated portion of the ring is useable.

There are several commonly known forms of annuloplasty rings. As a result there are three general divisions within the technology for annuloplasty rings. These divisions are stiff vs. flexible rings, partial vs. complete rings and adjustable vs. non-adjustable rings.

A conventional ring, disclosed in U.S. Pat. No. 4,055,861, completely surround the mitral or tricuspid valve annulus with the intent of supporting the entire annulus to prevent dilatation of the natural tissue. U.S. Pat. No. 4,144,046 discloses an early use of a flexible, partial ring. Subsequently, U.S. Pat. No. 4,164,046 disclosed an incomplete or partial ring that reinforces the posterior portion of the mitral valve annulus but does not extend across the anterior portion of the annulus. It was believed by many that the fibrous anterior portion of the annulus is not subject to dilatation, in contrast to the muscular posterior portion of the annulus. Operative time can be reduced with the implantation of a partial ring because fewer sutures are required to secure the ring to the native valve annular tissue. Further, there is some risk of damaging the aortic valve leaflets when placing sutures in the anterior portion of the mitral valve annulus. A partial ring limits this concern. Some surgeons have now abandoned the use of a partial ring because in some cases, patients have experienced dilation of the fibrous anterior tissue. As a result, many other surgeons now employ a complete ring.

Complete rings can be constructed at the operating table by the surgeon or purchased as a preconstructed product under the name Medtronic/Duran Annuloplasty Ring. Still, in many cases anterior ring reinforcement is not required, and therefore partial rings are used in some patients. Partial rings can be constructed at the operating table and are also commercially available under the name Baxter/Cosgrove Annuloplasty Ring.

In some cases, the decision to use a partial or complete ring is a matter of surgeon preference. In other cases, the condition of the patient's natural valve annulus is taken into account by the surgeon upon exposure of the valve during the operative procedure. The situation results in the need for both partial and complete rings to be available to the surgeons within any given hospital. This results in added expense for the hospital, both in terms of inventory investment and storage space required to make both types of rings available. Further, the surgeon must make the choice between a partial or complete ring before the first anchoring stitches are placed into the ring.

There are several other known annuloplasty ring devices. U.S. Pat. No. 3,656,185 discloses a cardiac valvular prosthesis, e.g., for the mitral valve, consisting solely of an annular or part-annular member adapted to fit against the base of the cusps of a human heart valve and suture means for securing the member in place. The prosthesis cooperates with the natural valve cusps of the patient to form the valve. This device is a semi-rigid ring with a shape that matches the correct anatomical shape of the native valve, allowing remodeling of the valve.

U.S. Pat. No. 4,042,979 discloses an adjustable valvuloplasty ring that comprises a C-shaped frame that is sized and shaped to extend about the circumference of the left atrioventricular orifice along the base of the anterior cusp of the mitral valve; an expandable sleeve connected to the frame that together therewith forms a closed annulus, the sleeve being adapted to extend about the remainder of the circumference of the orifice; and a drawstring running through the sleeve by which the sleeve may be contracted to constrict and remodel the orifice and secured in place to maintain such constriction. This ring is entirely flexible.

U.S. Pat. No. 4,290,151 discloses an adjustable annular prosthesis for use in the surgical correction of atrioventricular orifice defects. This ring allows adjustment of the two sides of the ring independently, rather than just allowing the reduction of the ring.

U.S. Pat. No. 4,489,446 discloses a heart valve prosthesis incorporating a dynamic stiffener element. The prosthesis is adapted for securing to the annulus of an atrioventricular valve and has the characteristic of allowing normal movement of the annulus during the cardiac cycle while providing mechanical support to the valve annulus so as to maintain the valve leaflets in proper physiological alignment. The stiffener element has a plurality of reciprocating members allowing it to be modifiable in shape so as to be capable of assuming the optimum shape for a particular heart valve. This ring is an adjustable semi-rigid ring.

In U.S. Pat. No. 5,061,277, a support for a natural heart valve is disclosed. The support is generally ring shaped and has a size and shape to fit against the natural heart valve annulus. A posterior length of the support is flexible, and an anterior length of the support is semi-rigid. Accordingly, when the support is implanted, the support can shape the heart valve annulus and the first length of the support allows contraction of the heart valve annulus therealong.

U.S. Pat. No. 5,104,407 discloses an annuloplasty ring prosthesis which is formed from a selectively flexible body element having at least one defined length about its circumference which is substantially rigid. The remainder of the body element gradually increases in flexibility. The body element is a substantially annular shaped body element which is designed to be sutured to the annulus of a heart valve. The body element is formed from a non-corrosive, anti-magnetic material, and is wrapped in a material through which sutures can be drawn to suture the prosthesis to the heart valve annulus. This ring includes an out-of-plane portion on the anterior side.

U.S. Pat. No. 5,306,296 discloses adjustable and flexible atrioventricular annuloplasty rings containing circumferential radiopaque markers with mitral and tricuspid valve variations. A variant of the ring for use in the mitral region incorporates a curved framework in the anterior segment. The framework member is to maintain the intratrigonal and anterior leaflet distance during implantation. It is curved to prevent aortic outflow tract obstruction. Two or more pairs of drawstrings allow adjustment of four segments of the posterior portion of the mitral valve annulus. The variant of the ring for use in the tricuspid region incorporates a single drawstring to allow adjustment of the posterior left and right segment of the ring at implantation. The flexible contractile body of the ring common to both variants is of a biocompatible cloth. This ring includes a semi-rigid anterior region and a flexible posterior portion. The size of the ring is adjustable on both sides of the annulus.

U.S. Pat. No. 5,593,424 discloses implanting a series of devices which reduce the circumference of a diseased cardiac valve annulus or vascular structure to the desired size. Specifically, disclosed is a method and apparatus that maintains the normal shape of a vessel or induces the vessel to regain its normal shape. This facilitates localized reduction of the annulus without the use of a ring or a partial ring.

U.S. Pat. No. 5,716,397 discloses a fully flexible annuloplasty ring which is temporarily stiffened during implantation by inserting a withdrawable stiffening wire into a lumen of the ring. The annuloplasty ring has a lumen which is able to hold the stiffener prior to and during insertion. The stiffener includes a portion extending out of the lumen which can be pulled to withdraw the stiffener once the implant has been implanted. Thus, this ring has a removable rigid element allowing the ring to be rigid at the time of implantation to facilitate suture placement and remodeling of the annulus.

Therefore, what is needed is an annuloplasty ring which would allow the surgeon to anchor the posterior portion of the ring and test the annulus as part of the decision process regarding the need for a complete or partial ring. If it is decided that the anterior portion of the ring is not needed, the surgeon may then elect to separate the anterior portion of the ring from the posterior portion.

SUMMARY

One embodiment, accordingly, provides an annuloplasty ring which is flexible and includes a separable anterior and posterior section. To this end, a separable annuloplasty ring comprises a first ring potion and a second ring portion. An interconnector member is used to interconnect the first and second ring portions. The interconnector member has at least one attachment to the first portion and at least one attachment to the second portion.

A principal advantage of this embodiment is that an annuloplasty ring is provided which is formed by two separable ring sections which can be used in complete ring form, or separated to be used in partial ring. The ring can also be provided in flexible form or stiffened form.

DETAILED DESCRIPTION

Figure 1:
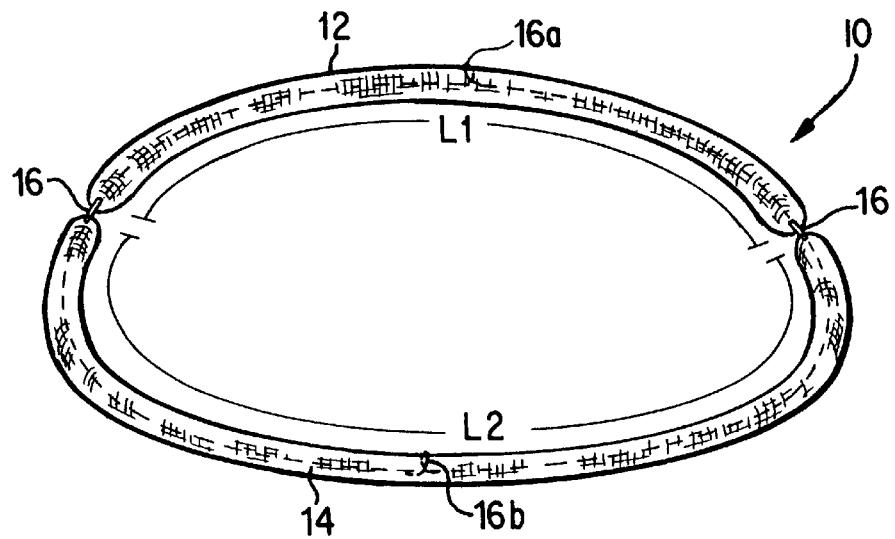
FIG. 1 is a plan view illustrating an embodiment of a separable annuloplasty ring.

A separable annuloplasty ring, FIG. 1, is generally designated 10 and includes a first flexible ring portion 12, a second flexible ring portion 14, and an interconnector member 16 for interconnecting the first ring portion 12 and the second ring portion 14. Interconnector member 16, which may be a polyester suture, is attached at 16a to first ring portion 12 and is attached at 16b to second ring portion 14. As illustrated, first ring portion 12 and second ring portion 14 are of unequal size, i.e first or anterior ring portion 12 is of a first length L1, and second or posterior ring portion 14 is of a second length L2, greater than L1. Such rings are often used as a support ring for a natural human heart valve such as a mitral valve, or sometimes used for tricuspid valve support. As such, ring 10 comprises a cardiac valvular prothesis for a heart valve.

Figure 2:
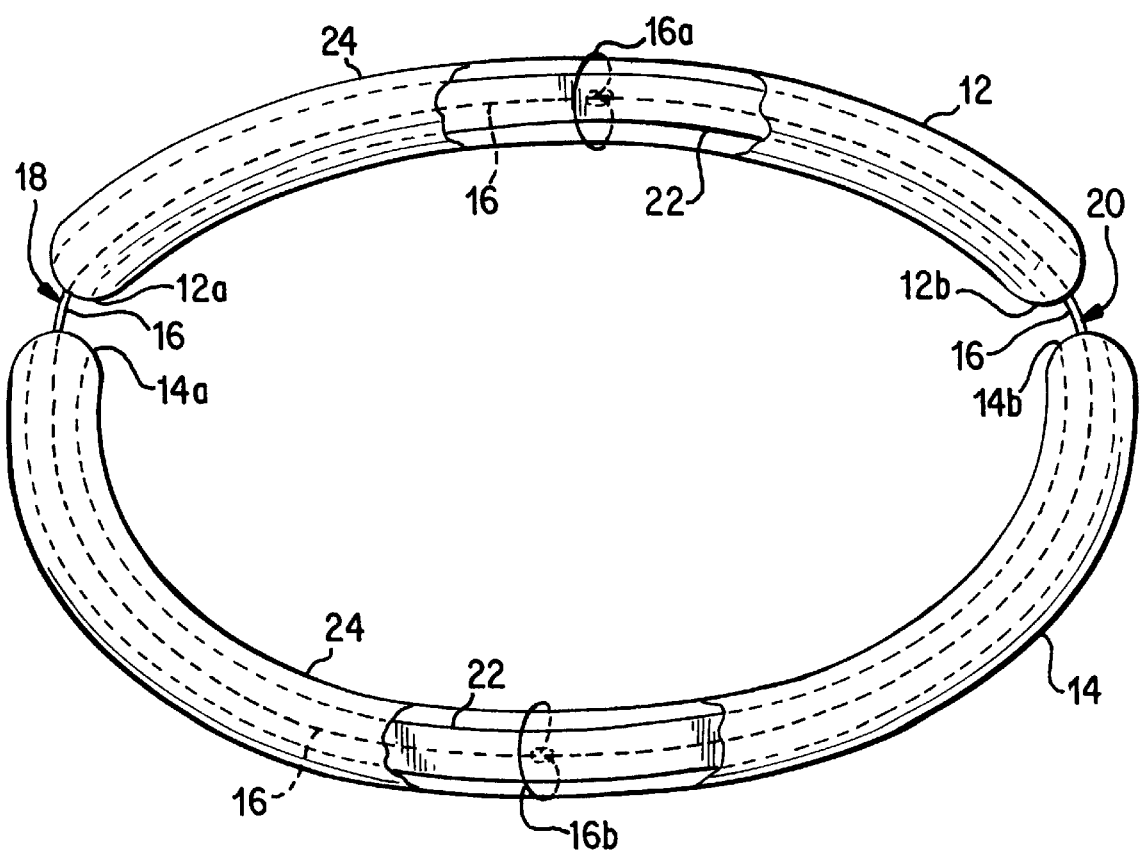
FIG. 2 is an enlarged plan view illustrating an embodiment of a flexible, separable annuloplasty ring.

First ring portion 12, FIG. 2, includes first and second terminal ends 12a and 12b, respectively. Similarly, second ring portion 14 includes first and second terminal ends 14a and 14b, respectively. The first terminal end 12a of first ring 12 is maintained adjacent the first terminal end 14a of second ring 14 by the interconnector member 16. Also, the second terminal end 12b of first ring 12 is maintained adjacent the second terminal end 14b of second ring 14 by the interconnector member 16. This is accomplished by looping or routing the interconnector member 16 through first ring portion 12 and through second ring portion 14. As such, the first terminal end 12a of first ring portion 12 is maintained adjacent the first terminal end 14a of second ring portion 14 to form a first interface 18. The second terminal end 12b of first ring portion 12 is maintained adjacent the second terminal end 14b of second ring portion 14 to form a second interface 20. Interconnector member 16 therefore extends across the first interface 18 and across the second interface 20. Construction of first ring portion 12 and second ring portion 14 of ring 10 includes an inner silicone tube member 22 within an outer polyester member 24. Interconnector member 16 extends through silicone tube member 22 and is looped and preferably knotted to the silicone tube member 22 and the polyester member 24 at the attachments 16a and 16b.

Figure 3:
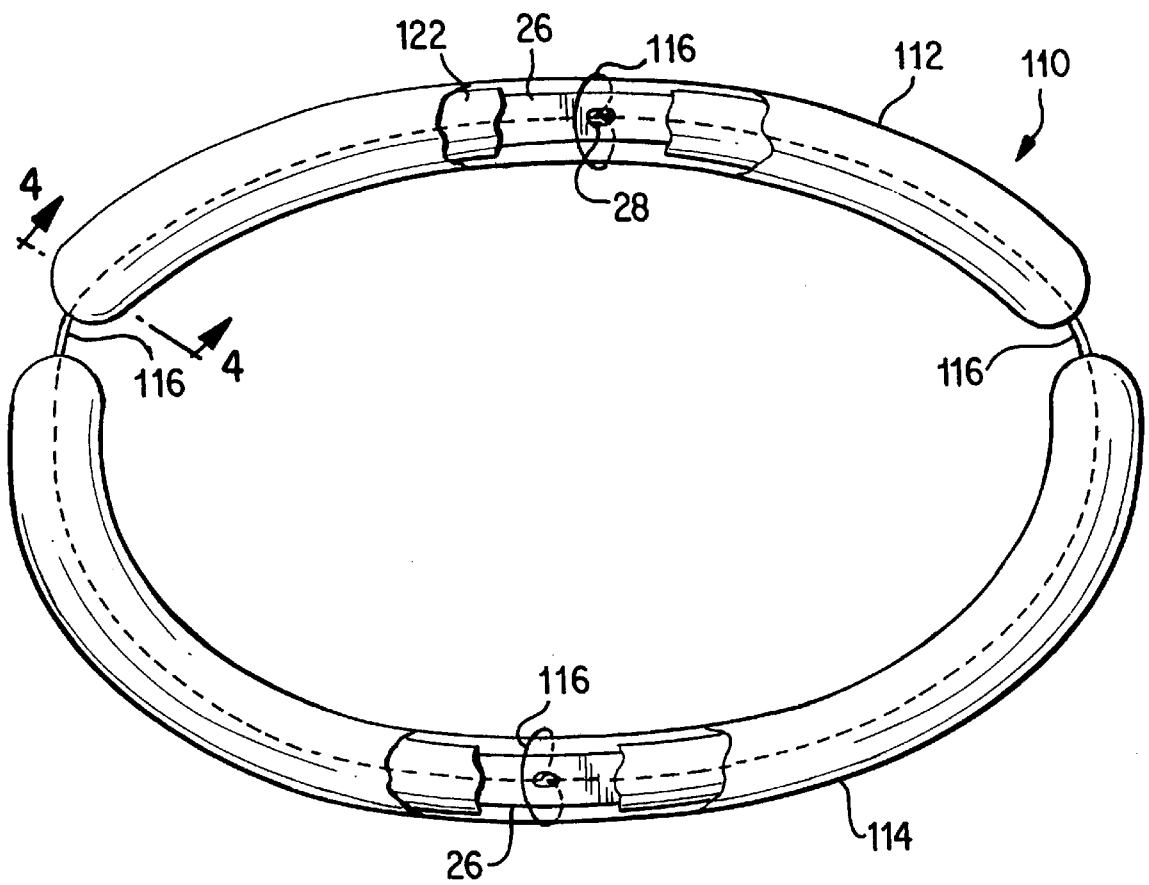
FIG. 3 is an enlarged plan view illustrating an embodiment of a flexible, separable annuloplasty ring including stiffener members.
Figure 4:
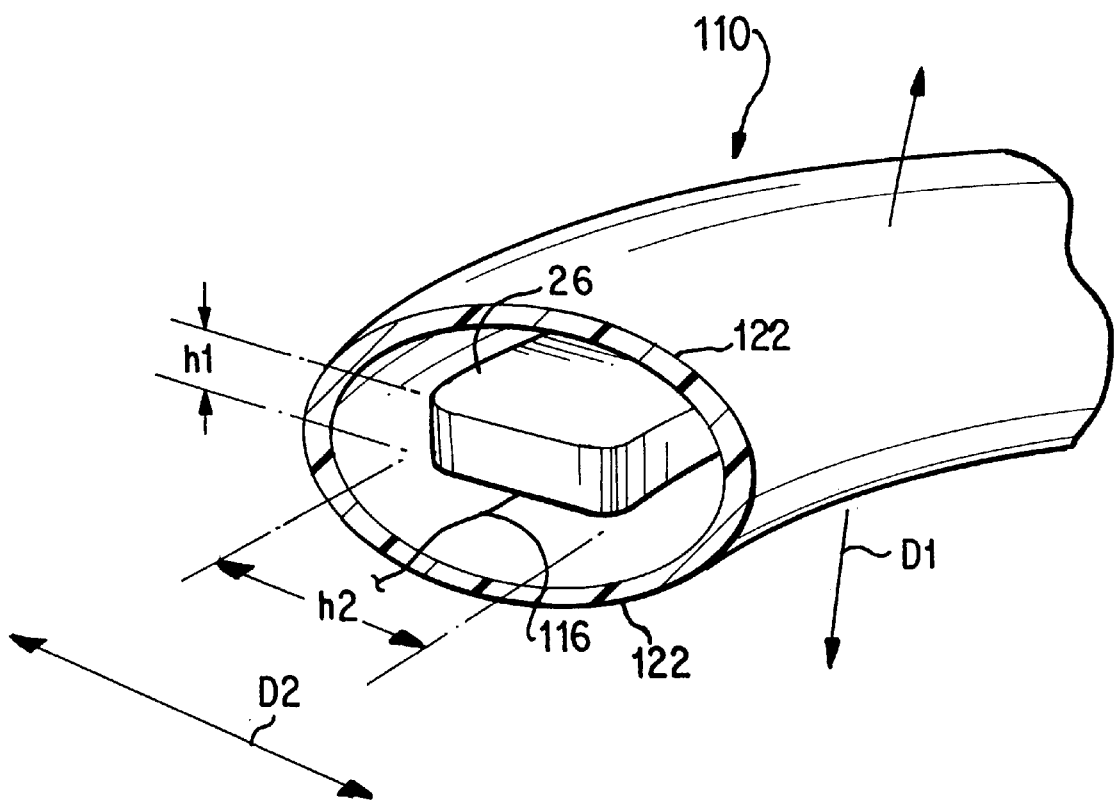
FIG. 4 is a partial isometric view taken along the line 4—4 of FIG. 3.
Figure 5:
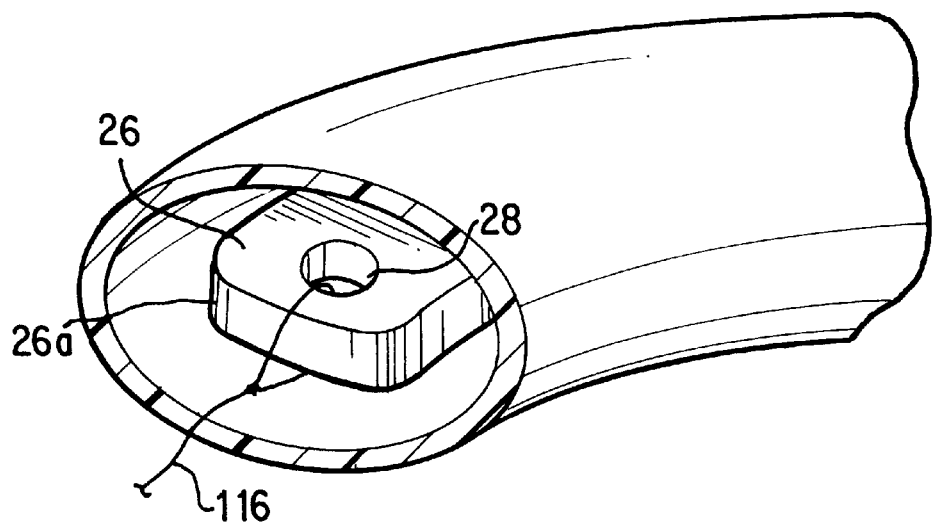
FIG. 5 is a partial isometric view illustrating another embodiment of a stiffener member.

A modified ring 110, FIG. 3, includes a first ring portion 112 and a second ring portion 114 including a semi-flexible titanium stiffener member 26. For example, stiffener member 26, may be provided in first ring portion 112 and in second ring portion 114. As such, the stiffener members 26 may be inserted within silicone tube member 122. A cross-sectional view, FIG. 4, illustrates that stiffener members 26 have a rectangular cross-section. This construction provides more or less stiffness in a desired direction. For example, dimension h1 is less than dimension h2, and therefore stiffness is greater in directions indicated by directional arrow D2, than in directions indicated by directional arrow D1. Ring 110 is constructed such that the addition of stiffener members 26 provides desired flexibility to accommodate natural heart pumping action. Furthermore, either one of the ring portions 112 or 114 may selectively include a respective stiffener member 26. Members 26 may also include apertures 28, FIG. 5, formed therein for securing interconnector member 116 thereto. The apertures 28 may be provided in an end 26a of members 26, or may be provided substantially at a mid-portion of the members 26, see FIG. 3.

Figure 6:
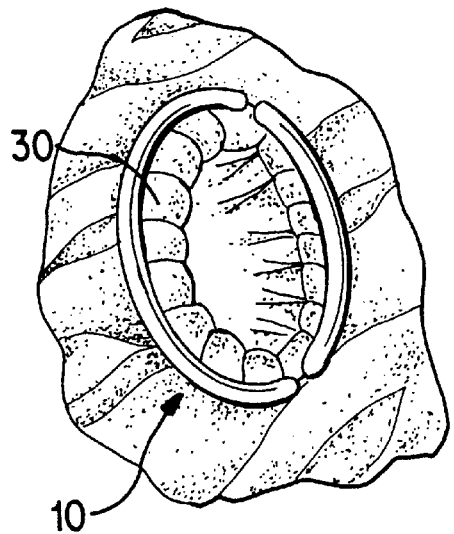
FIG. 6 is an isometric view illustrating a full ring attached to a heart valve.
Figure 7:
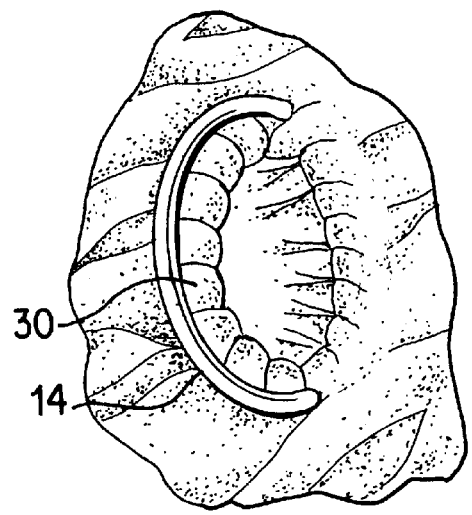
FIG. 7 is an isometric view illustrating a partial ring attached to the posterior side of the heart valve.
Figure 8:
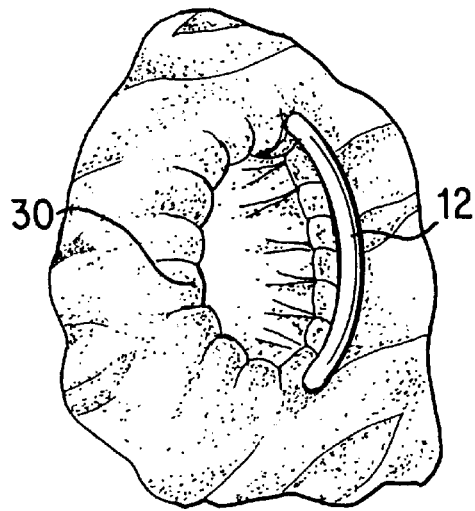
FIG. 8 is an isometric view illustrating a partial ring attached to the anterior side of the heart valve.

As a result of the foregoing embodiments, the surgeon may elect to use either a flexible ring 10, a semi-flexible stiffened ring 110 or a partially flexible and partially stiffened ring. In addition, a further option is available. The surgeon may use a full ring 10 to reinforce a heart valve 30, FIG. 6, or by severing the interconnector 16 at the interfaces 18 and 20, as described above, use either the larger, or posterior, ring portion 14 to reinforce valve 30, FIG. 7, or the smaller, or anterior, ring portion 12 to reinforce valve 30, FIG. 8. Once severed and installed by suturing the ring portion in the heart valve, tensioning on the ring portion will cause the severed end portions of the interconnector member to withdraw into the respective ring portions.

As it can be seen, the principal advantages of these embodiments are that they include a cloth covering to encourage tissue ingrowth. A braided suture core connects the anterior and posterior sections of the ring. A flexible polymer tube that surrounds the braided suture core, fits within the cloth covering. The polymer tube helps to provide shape to the ring and provides material for attachment of the surgeon's anchoring sutures. The suture is fully exposed in at least two interfaces to allow the surgeon to sever the suture, separating the posterior portion of the ring from the anterior portion of the ring. An embodiment of this invention includes the braided suture penetrating the polymer tube and possibly the cloth covering in at least one point of the posterior section and at least one point in the anterior section. As a result, the suture end is pulled back into the polymer tube when it is severed by the surgeon. This is done because the rough edges of an exposed suture can be a site for unwanted cell attachment. Thus, the terminal ends 12a, 12b, 14a and 14b are neatly sewn so that the ends of the suture withdraw into the ring segments.

In practice, if the surgeon is predisposed to use a partial ring on all patients he can easily remove a segment at any time without forcing the hospital to bear the cost of carrying a uniquely partial ring. The partial ring users will not inconvenience the other surgeons who might be predisposed toward using a complete ring or impose extra hospital carrying cost if this device is employed. In the case of surgeons who believe the choice of a partial or complete ring is a question of individual patient anatomy, they can, during the operative procedure, opt for either a complete or partial ring using this device. This single device can therefore serve surgeons who are currently employing a complete ring, surgeons who prefer a partial ring and surgeons who use both rings depending on individual patient anatomy.

This device may also be used by surgeons who prefer a stiffened ring. Stiffened rings offer the advantage of allowing the surgeon to restore the shape as well as the size of the native tissue annulus. Stiffened rings have two principle limitations. Rings that are stiffened on the posterior side have been reported to limit left ventricular contraction so the amount of blood ejected during systole is less than would be ejected with a flexible ring. Rings that are stiffened on the anterior side can push redundant tissue into the left ventricular outflow track causing phenomena known as systolic anterior motion (SAM). SAM can cause an increase in the aortic valve gradient forcing the heart to work harder to eject blood during systole. Rings with stiffened anterior portions and flexible posterior regions have been proposed to allow correction of annular shape without adversely effecting left ventricular contraction. A stiffened or reinforced tube or other structural modification on either the posterior or anterior sides of the ring could replace the flexible polymer tube in the above description. Use of a curved stiffened element on the anterior side would also allow for out of plane variations in the anterior portion of the annulus during systole as the ring would be naturally hinged at the interfaces where separation is facilitated by full exposure of the core suture, thus permitting out of plane movements of the hinged ring. This out of plane movement would only occur as part of conforming to the natural anatomy as with a fully flexible ring.

As a result, one embodiment provides a separable annuloplasty ring comprising a first ring portion, a second ring portion, and an interconnector member interconnecting the first and the second ring portions. The interconnector member has at least one attachment to the first portion and at least one attachment to the second portion.

Another embodiment provides a cardiac valvular prothesis for a heart valve comprising a segmented ring having a first ring segment and a second ring segment. Terminal ends of the first ring segment are retained adjacent terminal ends of the second ring segment by an interconnector member which extends between and interconnects the first and second ring segments. The interconnector member has a first connection to the first ring segment and a second connection to the second ring segment.

A further embodiment provides a support ring for a natural human heart valve comprising a first ring portion having opposite terminal ends and a second ring portion having opposite terminal ends. An interconnector member extends between and interconnects the first and second ring portions so as to maintain the opposite terminal ends of the first ring portions adjacent the opposite terminal ends of the second ring portion to form a segmented ring having a first and a second interface between the first and second ring portions.

Another embodiment provides a method of providing variable size reinforcing elements for a heart valve. A first ring segment is prepared and includes opposite terminal ends. A second ring segment is also prepared and includes opposite terminal ends. The terminal ends of the first ring segment are positioned adjacent the terminal ends of the second ring segment to form a first and a second interface between the first and second ring segments. An interconnector is inserted to extend through the first ring segment and the second ring segment so that the first and second interfaces are maintained between the first and second ring segments. The interconnector member is attached to the first ring segment and the second ring segment.

Although illustrative embodiments have been shown and described, a wide range of modifications, change and substitution is contemplated in the foregoing disclosure and in some instances, some features of the embodiments may be employed without a corresponding use of other features. Accordingly, it is appropriate that the appended claims be construed broadly and in a manner consistent with the scope of the embodiments disclosed herein.

What is claimed is:

1. A separable annuloplasty ring comprising:
   a first ring portion comprising a first tube member;
   a second ring portion comprising a second tube member;
   an interconnector member coupling the First and the second ring portions, said interconnector member extending through said first tube member and said second tube member, said annuloplasty ring being separable by severing said interconnector member without severing said first ring portion or said second ring portion.

2. The separable ring of claim 1 wherein the first ring portion further comprises a first outer covering and first and second terminal ends, and the second ring portion further comprises a second outer covering and first and second terminal ends.

3. The ring as defined in claim 1 wherein the first ring portion is of a first length and the second ring portion is of a second length, greater than the first length.

4. The separable ring of claim 1 wherein the first ring portion further comprises first and second terminal ends and the second ring portion further comprises first and second terminal ends, and wherein the first and second terminal ends of said first ring portion are coupled to the first and second terminal ends, respectively, of the second ring portion by the interconnector member.

5. The ring of claim 4 wherein the interconnector member is exposed sufficiently between said coupled first terminal ends and second terminal ends of said first and second ring portions for being severed without severing said first ring portion or said second ring portion.

6. The ring as defined in claim 5 wherein the first ring portion is of a first length and the second ring portion is of a second length, greater than the first length.

7. The ring of claim 2 wherein the first tube member and the second tube member each comprise a silicone tube and said first and second outer coverings each comprise a polyester knit tube.

8. A cardiac valvular prosthesis for a heart valve comprising:
- a segmented ring having a first ring segment comprising a first tube member having first and second terminal ends, and a second ring segment comprising a second tube member having first and second terminal ends, terminal ends of the first tube member being coupled to terminal ends of the second tube member by an interconnector member extending through and interconnecting the first and second tube members, the interconnector having a first connection to the first tube member and a second connection to the second tube member.

9. The prosthesis as defined in claim 8 wherein the interconnector is exposed sufficiently for being severed between said coupled terminal ends of said first and second tube members without severing said first ring segment or said second ring segment.

10. The prothesis as defined in claim 9 wherein the first ring segment and the length and the second ring segment is of a second length, greater than the first length.

11. The prosthesis of claim 8 wherein the first tube member and the second tube member each comprise a silicone tube within a polyester tube.

12. The prothesis as defined in claim 11 wherein the interconnector extends through the silicone tube of the first and second ring segments.

13. A support ring for a natural human heart valve comprising:
- a first ring portion comprising a first tube member and having opposite terminal ends;
- a second ring portion comprising a second tube member and having opposite terminal ends; and
- an interconnector member extending through said first tube member and said second tube member, said interconnector coupling the first and the second ring portions and maintaining the opposite terminal ends of the first ring portion adjacent the opposite terminal ends of the second ring portion to form a segmented ring separable by severing said interconnector member without severing said first ring portion or said second ring portion.

14. The support ring as defined in claim 13 wherein the heart valve is a mitral valve.

15. The support rings as defined in claim 13 wherein the heart valve is a tricuspid valve.

16. The support ring as defined in claim 15 wherein the first ring segment and the second ring segment are each formed of a silicon tube within a polyester tube, and a shape stiffener member.

17. The support ring as defined in claim 13 wherein the interconnector is a suture.

* * * * *